United States Patent [19]

Taguchi et al.

[11] 4,229,597

[45] Oct. 21, 1980

[54] PROCESS FOR THE PREPARATION OF RESORCIN

[75] Inventors: Thoru Taguchi, Waki; Tokinori Ago, Ohtake; Isao Hashimoto, Waki, all of Japan

[73] Assignee: Mitsui Petrochemical Industries Ltd., Tokyo, Japan

[21] Appl. No.: 948,630

[22] Filed: Oct. 3, 1978

[30] Foreign Application Priority Data

Oct. 8, 1977 [JP] Japan .................................. 52-120507

[51] Int. Cl.$^2$ ........................ C07C 37/08; C07C 39/08
[52] U.S. Cl. ................................................. 568/768
[58] Field of Search .......................................... 568/768

[56] References Cited

U.S. PATENT DOCUMENTS

| | | | |
|---|---|---|---|
| 2,784,238 | 3/1957 | Jacobs | 568/768 |
| 3,305,590 | 2/1967 | Pollitzer | 568/768 |

*Primary Examiner*—Werren B. Lone
*Attorney, Agent, or Firm*—Sherman & Shalloway

[57] ABSTRACT

A process for the preparation of resorcin comprising decomposing meta-diisopropylbenzene dihydroperoxide in the presence of a synthetic silica-alumina catalyst, wherein the concentration of water in the reaction system is maintained at 0.3 to 1.0% by weight, is disclosed.

6 Claims, No Drawings

PROCESS FOR THE PREPARATION OF RESORCIN

BACKGROUND OF THE INVENTION (1) Field of the Invention

The present invention relates to a process for preparing resorcin by acid decomposition of meta-diisopropylbenzene dihydroperoxide (hereinafter referred to "m-DHP"). More particularly, the invention relates to a process for preparing resorcin in a high yield by conducting this decomposition reaction in the presence of a specific amount of water.

(2) Description of the Prior Art

A process for preparing phenols and ketones by acid decomposition of hydroperoxides of tertiary-alkylbenzenes has been known from old. Also a process for preparing resorcinol from meta-diisopropylbenzene dihydroperoxide ($\alpha,\alpha,\alpha',\alpha'$-tetramethylxylyl dihydroperoxide) is disclosed in, for example, the specification of U.S. Pat. No. 3,305,590 to Pollitzer et al. Further, various catalysts for this reaction have been proposed, and in the above specification, it is disclosed that a synthetic silica-alumina catalyst is used.

In the preparation of resorcin by acid decomposition of m-DHP, side reactions are caused more readily than in case of acid decomposition of other hydroperoxides of tertiary-alkylbenzenes. Accordingly, it is difficult to obtain resorcin in a high yield. For example, under ordinary acid decomposition conditions, reaction between resulting phenols and ketones is hardly caused to occur and the side reaction can be substantially neglected. On the other hand, since resorcin is more highly reactive than other phenols, it readily forms a condensation product with acetone. Further, resorcin readily reacts with carbinols or olefins formed as by-products to form high-boiling-point products. Therefore, according to the conventional processes, it is very difficult to prepare resorcin in a high yield by acid decomposition of m-DHP.

In general, m-DHP is prepared by liquid phase air oxidation of m-diisopropylbenzene (M-DIPB) and/or m-diisopropylbenzene monohydroperoxide (m-MHP). If m-DHP can be subjected to acid decomposition not in the completely pure state but in the state containing small amounts of other oxidation products, the expenses required for separation and purification of m-DHP will be saved or reduced and the production of resorcin will be performed industrially advantageously. However, according to the conventional techniques, it is more difficult to obtain resorcin in a high yield when such impure m-DHP is employed.

BRIEF SUMMARY OF THE INVENTION

As a result of our research on acid decomposition of meta-diisopropylbenzene dihydroperoxide, it was found that when a synthetic silica-alumina is selected as the catalyst and water is made present in the reaction system in a specific amount, namely 0.3 to 1.0% by weight based on the total starting mixture, decomposition of m-DHP can be performed at an appropriate reaction rate while controlling occurrence of the above-mentioned side reactions and therefore, resorcin can be prepared in a high yield. We further found that when the acid decomposition is carried out in the presence of the above-mentioned specific amount of water, impure m-DHP obtained by liquid phase air oxidation of m-DIPB and m-MHP can be directly used as the starting material and resorcin can be prepared in a high yield even from such impure m-DHP.

OBJECTS OF THE INVENTION

It is therefore a primary object of the present invention to provide an improved process in which resorcin can be prepared in a good yield from meta-diisopropylbenzene dihydroperoxide.

Another object of the present invention is to provide a process in which resorcin can be prepared in a good yield by using directly meta-diisopropylbenzene dihydroperoxide containing impurities as the starting material to be subjected to acid decomposition.

In accordance with the fundamental aspect of the present invention, there is provided a process for the preparation of resorcin comprising decomposing meta-diisopropylbenzene dihydroperoxide in the presence of a synthetic silica-alumina catalyst, wherein the concentration of water in the reaction system is maintained at 0.3 to 1.0% by weight.

In accordance with one preferred embodiment of the present invention, there is provided a process for the preparation of resorcin comprising contacting impure meta-diisopropylbenzene dihydroperoxide obtained by liquid phase air oxidation of meta-diisopropylbenzene and/or meta-diisopropylbenzene monohydroperoxide, with a synthetic silica-alumina catalyst having a silica content of 60 to 95% by weight and a specific surface area of at least 100 m$^2$/g, under refluxing conditions in a mixed solvent of a ketone and an aromatic hydrocarbon containing 0.3 to 1.0% by weight of water based on the total starting mixture.

DETAILED DESCRIPTION OF THE INVENTION

As is well-known in the art, meta-diisopropylbenzene dihydroperoxide (m-DHP) that is used in the present invention can be prepared by liquid phase air oxidation of m-diisopropylbenzene (m-DIPB) and/or m-diisopropylbenzene monohydroperoxide (m-MHP). The oxidation product obtained by such air oxidation includes not only m-DHP but also other oxidation by-products and unreacted compounds. In general, this oxidation product contains 10 to 35% by weight of m-MHP based on m-DHP and in some case, it further contains such impurities as $\alpha,\alpha$-dimethyl-m-hydroxyisopropylbenzyl monohydroperoxide and $\alpha,\alpha$-dimethyl-m-acetobenzyl monohydroperoxide. These impurities readily react with resorcin under decomposition conditions. Therefore, according to the conventional processes, it is difficult to obtain resorcin in a satisfactory yield unless pure m-DHP isolated from such oxidation product is employed. In contrast, according to the present invention, resorcin can be obtained in a good yield even when such impure oxidation product is directly used as it is or after parts of impurities have been removed. Namely, in the present invention, the above-mentioned oxidation product can be used directly as the starting material without separation of oxidation by-products or after parts of them have been removed. Of course, m-DHP isolated from the product of oxidation of m-DIPB or M-MHP can be used as the starting material in the process of the present invention. Also in this case, resorcin can be obtained in a much higher yield than those attainable in the conventional processes.

In the process of the present invention, acid decomposition reaction is advantageously carried out in an appropriate inert solvent. In general, ketones such as acetone, methylethyl ketone and methylisobutyl ketone and hydrocarbons such as benzene, toluene, xylene and ethylbenzene are used. In the present invention, it is especially preferred that the decomposition be carried out in a mixed solvent comprising a ketone and an aromatic hydrocarbon.

The concentration of m-DHP in the starting mixture is not particularly critical, but it is preferred that the concentration of m-DHP be in the range of from 15 to 35% by weight.

The synthetic silica-alumina that is used in the present invention is known as a catalyst, and the process for the preparation of this synthetic silica-alumina catalyst is not particularly critical. For example, there can be used a silica-alumina catalyst prepared by the deposition process in which an alumina hydrate is formed in a suspension of a hydrogel of silica and is deposited on the silica hydrogel to form a silica-alumina hydrogel and the hydrogel is dehydrated and dried, a synthetic silica-alumina catalyst prepared by the mixing process in which a silica hydrogel is mixed with an alumina hydrogel and the mixture is dehydrated and dried, and a synthetic silica-alumina catalyst prepared by the coprecipitation process in which a silica-alumina hydrogel is coprecipitated from a mixed solution of a water-soluble silicate and a water-soluble aluminium salt and the hydrogel is hydrated and dried. It is preferred to use a synthetic silica-alumina having a silica content of 60 to 95% by weight and a specific surface area of at least 100 $m^2/g$. In general, it is preferred that the synthetic silica-alumina be calcined at a temperature of about 300° to about 700° C. before the acid decomposition is carried out according to the present invention. The silica-alumina catalyst can be used in the powdery form or in the granular form. The silica-alumina catalyst is made present in a known catalytic amount. In general, the catalyst is used in an amount of 50 to 200% by weight based on m-DHP.

In the present invention, it is very important that water is made present in the reaction system at a concentration of 0.3 to 1.0% by weight, preferably 0.4 to 0.9% by weight. This condition is critical for preparing resorcin at a high reaction speed in a high yield while controlling the above-mentioned side reactions. When the water concentration is below the above range, the reaction speed is high but the yield of resorcin is low because side reactions are readily caused. If the water concentration exceeds 1.0% by weight, the reaction speed is drastically reduced and even if the reaction time is prolonged, the yield of resorcin is not improved. The phenomenon that resorcin can be prepared in a high yield when the water concentration in the reaction system is maintained at 0.3 to 1.0% by weight is a peculiar phenomenon observed only when a synthetic silica-alumina catalyst is employed, and if sulfuric acid is used as the catalyst, even when the above condition of the water concentration is satisfied, it is impossible to obtain resorcin in a high yield.

In the present invention, the reaction is carried out at 20° to 120° C., preferably at 50° to 100° C. The reaction time is changed depending on the temperature, but in general, conditions such as the amount of the catalyst and the m-DHP concentration are selected so that the reaction is completed within 0.5 to 5 hours. If the reaction is carried out in a solvent such as mentioned above and refluxing conditions are adopted, the control or adjustment of the reaction conditions can be remarkably facilitated.

The acid decomposition of m-DHP may be carried out batchwise or according to a continuous process. For example, there can be adopted a method in which m-DHP is passed through a reaction vessel packed with a synthetic silica-alumina and a method in which the reaction is carried out while feeding m-DHP into a reaction vessel where a synthetic silica-alumina is dispersed in an inert solvent as described above under agitation. It is advantageous that m-DHP is fed to a reaction vessel in the form of a solution in a solvent as described above. Water necessary for the reaction may be directly added to the starting mixture or it may be added in the state diluted with the solvent. In other words, means for addition of water is not particularly critical in the present invention, so far as water is present in the starting mixture at the above-mentioned specific concentration. In order to facilitate the adjustment of the water concentration and distribute water uniformly in the starting mixture, it is preferred to feed water in the form of a water-acetone mixture.

Isolation of resorcin from the reaction mixture can be accomplished easily by known means such as distillation under reduced pressure.

As will be apparent from the foregoing illustration, according to the present invention, there is attained a great industrial advantage that resorcin can be prepared in a high yield from m-DHP.

The present invention will now be described in detail by reference to the following Examples that by no means limit the scope of the Invention.

EXAMPLES 1 TO 4 AND COMPARATIVE EXAMPLES 1 TO 4

A 100 ml capacity 4-neck flask equipped with a stirrer, a thermometer and a cooler was charged with 15 ml of a mixed solvent of toluene and acetone (the mixing weight ratio being 3/7) and 4.5 g of a commercially available silica-alumina (calcined at 680° C. for 2 hours; silica content=87% by weight; specific surface area=450 $m^2/g$). Then, 19.2 g of a toluene-acetone solution of a product of oxidation of m-DIPB having a composition shown in Table 1 and a predetermined amount of a water-acetone mixture (the weight ratio being 5/95) were simultaneously added to the charge of the flask under heating and reflux over a period of 10 minutes. Acid decomposition was carried out for a predetermined time while maintaining the water concentration at a level indicated in Table 2. The amount of the unreacted hydroxyperoxides left in the reaction product was determined according to the iodimetry and the amount of resorcin was determined by the gas chromatography. Obtained results are shown in Table 2.

TABLE 1

| Component | Content (% by weight) |
|---|---|
| m-DHP | 23.0 |
| m-MHP | 6.1 |
| Toluene | 19.4 |
| Acetone | 45.4 |
| Others | 6.1 |

TABLE 2

|  | Water Concentration (% by weight) in Reaction System | Reaction Time (hours) | Conversion (% of Hydroperoxides*) | Yield (%) of Resorcin** |
| --- | --- | --- | --- | --- |
| Example 1 | 0.3 | 1 | 99.7 | 83 |
| Example 2 | 0.7 | 1 | 99.7 | 85 |
| Example 3 | 0.9 | 1 | 99.5 | 84 |
| Example 4 | 1.0 | 1 | 99.2 | 83 |
| Comparative Example 1 | 0.2 | 0.5 | 99.7 | 74 |
| Comparative Example 2 | 0.2 | 1 | 99.9 | 73 |
| Comparative Example 3 | 1.1 | 2 | 99.4 | 73 |
| Comparative Example 4 | 1.4 | 3 | 99.2 | 74 |

Note
*conversion of the total hydroperoxide groups of both m-DHP and m-MHP
**yield of resorcin based on m-DHP

EXAMPLES 5 TO 6 AND COMPARATIVE EXAMPLES 5 TO 6

Acid decomposition was carried out for a predetermined time by using a solution of 4.4 g of m-DHP having a purity of 99.5% in 14.8 g of toluene-acetone (weight ratio=3/7) in the same manner as described in Example 1 while maintaining the water concentration in the reaction system at a level indicated in Table 3 by changing the amount fed of the water-acetone mixture. Obtained results are shown in Table 3.

TABLE 3

|  | Water Concentration (% by weight) in Reaction System | Reaction Time (hours) | Conversion (%) of m-DHP | Yield (%) of Resorcin |
| --- | --- | --- | --- | --- |
| Example 5 | 0.4 | 1 | 99.7 | 98 |
| Example 6 | 0.9 | 1 | 99.6 | 98 |
| Comparative Example 5 | 0.2 | 0.5 | 99.8 | 91 |
| Comparative Example 6 | 1.1 | 2 | 99.3 | 92 |

COMPARATIVE EXAMPLE 7

Acid decomposition was carried out in the same manner as in Example 2 except that 0.096 g of 98% $H_2SO_4$ was used as the catalyst instead of the silica-alumina. The conversion of the hydroperoxides was 99.6% and the yield of resorcin was 72%.

What we claim is:

1. In a process for the preparation of resorcin by decomposing meta-diisopropylbenzene dihydroperoxide in the presence of a synthetic silica-alumina catalyst, the improvement comprising feeding said meta-diisopropylbenzene dihydroperoxide and water under agitation into a reaction vessel filled with a dispersion of said synthetic silica-alumina catalyst in a mixed solvent comprising a major amount of acetone and a minor amount of an aromatic hydrocarbon, and decomposing said meta-diisopropylbenzene dihydroperoxide under reflux conditions in the presence of 0.4 to 0.9% by weight of water based on the total starting mixture.

2. A process according to claim 1 wherein the meta-diisopropylbenzene dihydroperoxide is a mixture containing impurities, which is obtained by liquid phase air oxidation of meta-diisopropylbenzene and/or meta-diisopropylbenzene monohydroperoxide.

3. A process according to claim 3 wherein water is fed to the reaction system in the form of a water-acetone mixture.

4. A process according to claim 1 wherein the synthetic silica-alumina has a silica content of 60 to 95% by weight and a specific surface area of at least 100 m²/g.

5. A process according to claim 1 wherein the decomposition of the meta-diisopropylbenzene dihydroperoxide is carried out at a temperature of 20° to 120° C. for 0.5 to 5 hours.

6. A process for the preparation of resorcin comprising contacting impure meta-diisopropylbenzene dihydroperoxide obtained by liquid phase air oxidation of meta-diisopropylbenzene and/or meta-diisopropylbenzene monohydroperoxide, with a dispersion of a synthetic silica-alumina catalyst having a silica content of 60 to 95% by weight and a specific surface area of at least 100 m²/g, under refluxing conditions in a mixed solvent of a ketone selected from the group consisting of acetone, methylethylketone and methylisobutyl ketone and an aromatic hydrocarbon selected from the group consisting of benzene, toluene, xylene and ethylbenzene containing 0.3 to 1.0% by weight of water based on the total starting mixture.

* * * * *

UNITED STATES PATENT AND TRADEMARK OFFICE
CERTIFICATE OF CORRECTION

PATENT NO. : 4,229,597
DATED : October 21, 1980
INVENTOR(S) : TAGUCHI, ET AL.

It is certified that error appears in the above—identified patent and that said Letters Patent is hereby corrected as shown below:

Claim 3, line 1, delete "3" and insert -- 1 --.

Signed and Sealed this

Seventeenth Day of February 1981

[SEAL]

Attest:

RENE D. TEGTMEYER

Attesting Officer

Acting Commissioner of Patents and Trademarks